United States Patent [19]

Alphin et al.

[11] 4,025,624

[45] May 24, 1977

[54] PHENYLALKYLAMINES AND PHENYLALKYLUREAS IN COMBINATIONS TO SUPPRESS GASTRIC BLEEDING IN ASPIRIN THERAPY

[75] Inventors: Reevis Stancil Alphin; William John Welstead, Jr., both of Richmond, Va.

[73] Assignee: A. H. Robins Company, Incorporated, Richmond, Va.

[22] Filed: Nov. 18, 1975

[21] Appl. No.: 633,042

[52] U.S. Cl. .................. 424/233; 424/232; 424/322
[51] Int. Cl.² .............. A61K 31/17; A61K 31/615; A61K 31/625
[58] Field of Search ................ 424/233, 322

Primary Examiner—Stanley J. Friedman

[57] ABSTRACT

Novel pharmaceutical methods, combinations and compositions for reducing gastric bleeding during aspirin therapy for inflammation are disclosed. Compounds used in combination with aspirin are phenylalkylamines and phenylalkylureas having the formula:

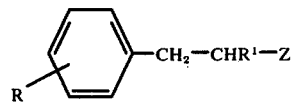

wherein Z is selected from the group consisting of $-NHR^2$ or

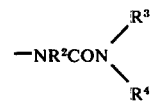

and R is selected from the group consisting of hydrogen, halogen, lower-alkoxy and trifluoromethyl and $R^1$, $R^2$, $R^3$ and $R^4$ are selected from the group consisting of hydrogen and lower-alkyl, where $R^3$ and $R^4$ taken together with the adjacent nitrogen atom may form a heterocyclic ring selected from the group of piperidino, pyrrolidino, piperazino, and morpholino.

14 Claims, No Drawings

PHENYLALKYLAMINES AND PHENYLALKYLUREAS IN COMBINATIONS TO SUPPRESS GASTRIC BLEEDING IN ASPIRIN THERAPY

BACKGROUND OF THE INVENTION

The present invention relates to novel methods, combinations and compositions for reducing gastric bleeding during aspirin therapy in the treatment of inflammation. More particularly, the invention relates to methods, combinations and compositions therefor, of reducing gastric bleeding frequently found attendant to aspirin therapy in mammalian subjects which comprises administering in combination with aspirin, an effective amount of certain phenylalkylamines and phenylalkylureas.

There are various diseases in chronic and acute form which afflict mammals and for which aspirin therapy is indicated and prescribed. In many instances a high incidence of bleeding and ulceration results as side effects from the administration of aspirin for its anti-inflammatory effect. For example, high dosages of aspirin are administered to mammalian subjects in the treatment of inflammatory conditions associated with diseases generally described as rheumatic or arthritic types, but attendant to the beneficial effects of reduction of inflammation and swelling of joints and tissue in various parts of the mammalian body are detrimental effects of ulceration and bleeding with appreciable blood loss in the stomach. The need to overcome these side effects due to aspirin administration is well recognized in the fields of human and veterinary medicine and that in some cases the continual loss of blood cannot be tolerated. Oftentimes, aspirin therapy must be terminated, thus giving rise to exposure, in the search for other satisfactory chemotherapy, to the potential danger from certain other anti-inflammatory agents which may cause even more severe ulceration and perforation in certain parts of the gastrointestinal tract. Thus, the accomplishment of the present invention in reducing bleeding due to aspirin therapy can be readily appreciated by one skilled in the art, particularly when it is realized that conditions of intolerance to aspirin because of induced ulceration and bleeding can be avoided by the methods, combinations and compositions of this invention.

Indicative of the state of the art have been attempts to find combinations which would allow administration of aspirin for its full therapeutic effect as an anti-inflammatory drug. Coprecipitates of aspirin with lignosulfonate (Brit. Pat. No. 1,345,358) with tannic acid (Brit. Pat. No. 1,345,359) and tea (Belg. Pat. No. 806,392) have all shown reduced irritation in the cat stomach.

Cyclobenzaprine combined with aspirin for muscle relaxing effect in animals has been disclosed in British Pat. No. 1,334,326. The dosages of both cyclobenzaprine and aspirin are said to be subclinical and because less of these drugs is used, side effects are reduced. In the instant invention aspirin is administered in full dosage amount for its anti-inflammatory effect and the phenylalkylamines or phenylalkylureas are co-administered to reduce the bleeding normally attendant to full dosage amounts of aspirin.

SUMMARY OF THE INVENTION

The present invention provides methods of treating mammals, including humans, for symptomatic conditions of inflammation for relief of which aspirin therapy is generally indicated but cannot be most effectively accomplished because of accompanying side effects due to gastric irritation caused by the aspirin. We have discovered that when certain phenylalkylamines or phenylalkylureas are present systemically in the mammalian body during the period of time the mammalian stomach is exposed to aspirin following oral ingestion of aspirin, bleeding and ulceration in the stomach are greatly reduced. In general, the method of this invention comprises administering daily normally effective amounts of from about 20 to about 200 mg/kg body weight aspirin in single or divided doses for the control of symptomatic conditions of inflammation and concomitantly administering from about 0.1 to about 100 mg/kg body weight of the phenylalkylamines or phenylalkylureas in single or divided doses of this invention, said phenylalkylamines and phenylalkylureas being administered at least during the time period aspirin is administered. The weight ratio of phenylalkylamines and phenylalkylureas to aspirin required for its intended effect does not exceed 0.5 to 1; i.e., a maximum for 33% phenylalkylamine or phenylalkylurea, the effective required range being 0.005 to 0.5 parts by weight phenylalkylamine or phenylalkylurea per part by weight of aspirin. On the basis of 100 parts of the combination, phenylalkylamine or phenylalkylurea will therefore be from about 0.5 to 33 parts and the aspirin will be about 67 to 99.5 parts. In order to more effectively reduce or suppress initial bleeding caused by aspirin, the phenylalkylamine and phenylalkylurea compounds may be preadministered about 1 to 2 hours prior to the start of aspirin therapy to allow blood levels of the compounds to build up to protective levels and thus prevent initial excess bleeding in sensitive subjects. When the phenylalkylamines and phenylalkylurea compounds and aspirin are administered simultaneously but without preadministration, there will be an initial period of time before blood level of the compounds has built sufficiently to give maximum protection against ulceration and bleeding; however, the bleeding will subside as blood levels build on continued use of the combination. The compounds may be administered orally in physical combination with aspirin with or without adjuvants or carriers, or in separate dosage form from aspirin. In order to guard against neglect of administering the phenylalkylamines or phenylalkylurea compounds, the surest protection is obtained using the physical combination and for this reason as well as for convenience, the invention is also concerned with compositions containing the combination. In general, the compositions contain the proportions of the combination suitable for control of bleeding and ulceration outlined above for combined dosage forms and will contain about 0.005 to about 0.5 parts by weight of phenylalkylamine or phenylalkylurea compounds per part of aspirin for effective remedial control of ulceration and bleeding in the mammalian stomach. These novel compositions can therefore contain on a percentage basis compounds of Formula I from about 0.5 to about 33% by weight of a compound of Formula I and from about 67 to about 99.5% aspirin. Preferably, the compositions contain on a weight percentage basis of aspirin and the phenylalkylamine or phenylalkylurea about 0.5 to 25% compound of Formula I and 75 to 99.5% aspirin. Generally, the choice of ratio will depend on the compound of Formula I chosen for a particular mammalian species.

The compounds of this invention useful in combination in pre-therapy and co-therapy with aspirin for anti-inflammatory treatment of mammals including humans have the formula:

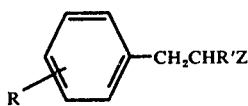

Formula I wherein;
Z is selected from the group consisting of —$NHR^2$ or

R is selected from the group consisting of hydrogen, chlorine, bromine, fluorine, lower alkyl, lower alkoxy, or trifluoromethyl, and $R^1$, $R^2$, $R^3$, and $R^4$ are selected from the group consisting of hydrogen and lower-alkyl where $R^3$ and $R^4$ taken together with the adjacent nitrogen atom may form a heterocyclic ring selected from the group consisting of piperidino, pyrrolidinyl, piperazino, and morpholino and the pharmaceutically acceptable acid addition salts thereof.

The primary object of this invention is to provide a method of treating inflammation with aspirin in mammals, including humans, wherein the side effects of incidence of gastric bleeding and ulceration are greatly reduced in systemic action by administration of ulcer ameliorating compounds in conjunction with the aspirin which are certain phenylalkylamine and phenylalkylurea compounds.

Another object of this invention is to provide a method of treating inflammation with aspirin; i.e., aspirin therapy, wherein the incidence of bleeding and ulceration is decreased by concomitant or co-administration of certain phenylalkylamine and phenylalkylurea compounds.

Another object of this invention is to provide a method of reducing intestinal ulceration due to aspirin therapy by preadministration of certain phenylalkylamine and phenylalkylurea compounds prior to co-administration of a combination of aspirin and the phenylalkyl compounds.

Another object of this invention is to provide pharmaceutical combinations of aspirin and certain phenylalkylamine and phenylalkylurea compounds in physical combination in unit dosage forms for co-administration which are useful for treating inflammation with reduced incidence of harmful bleeding and ulceration.

Another object of this invention is to provide a protection by systemic means to the stomach of mammals against bleeding and ulceration caused by high doses of aspirin by administering the phenylalkylamine and phenylalkylurea compounds of this invention prior to and during the time of aspirin administration.

Still other objects will occur to one skilled in the art from the description which follows:

DETAILED DESCRIPTION OF THE INVENTION

According to the method of this invention which comprises combining the administration of phenylalkylamines and phenylalkylurea compounds of Formula I and aspirin in ratios on a 100 parts basis of about 0.5 to 33 parts of phenylalkylamines and phenylalkylurea compounds of Formula I and about 67 to 99.5 parts of aspirin, symptomatic relief of inflammation in mammals, including humans, is obtained with reduced side effects in the stomach.

Included among the phenylalkylamines and phenylalkylurea compounds of Formula I useful in the practice of this invention are:

1. 2-ethylamino-1-(3-trifluoromethylphenyl)propane
2. 2-amino-1-(3-trifluoromethylphenyl)propane
3. 1-methyl-1-(α-methylphenethyl)urea
4. 1-(α-methyl-3-trifluoromethylphenethyl)urea
5. 1-ethyl-1-(α-ethyl-3-trifluoromethylphenethyl)urea
6. 1,3-diethyl-1-(α-methyl-3-trifluoromethylphenethyl)urea
7. 3-ethyl-1-methyl-1-(α-methylphenethyl)urea
8. 3-ethyl-1-(α-methyl-3-trifluoromethylphenethyl)urea
9. 1-(α-methyl-3-chlorophenethyl)urea
10. 1-(α-methyl-3-bromophenethyl)urea
11. 1-(α-methyl-3-fluorophenethyl)urea
12. 1-(α-ethyl-3-trifluoromethylphenethyl)urea
13. 1-(α-methyl-2-methoxyphenethyl)urea
14. 1-(3-trifluoromethylphenethyl)urea
15. 1-(4-chlorophenethyl)urea
16. 2-ethylamino-1-(2 methoxyphenyl)propane
17. 2-amino-1-(3 chlorophenyl)propane The term "lower alkyl" as used herein indicates straight and branched chain hydrocarbon radicals of up to four carbon atoms and is exemplified by such groups as methyl, ethyl, n-propyl, isopropyl, n-butyl, isobutyl and tertiarybutyl and the like. A "lower alkoxy" group has the formula -O-lower alkyl.

The phenylalkylamines useful in this invention are well known in the art and include fenfluramine and norfenfluramine.

The phenylalkylurea compounds mentioned hereinabove may be prepared by reacting the appropriately substituted phenylalkylamines with nitrourea and lower-alkyl isocyanates or carbamoyl chloride, according to procedures well known in the art.

EXAMPLES 1 AND 2 (PHENYLALKYLAMINES)

The prevention of aspirin-induced bleeding in rats was determined by the following procedure. Female Sprague-Dawley rats weighing 150–180 g. were fasted for 24 hours on wire and divided into groups of six animals each. The rats were anesthetized and a ligature placed at the pyloricduodenal junction. Groups serving as controls received normal saline (4.0 ml/kg, i.p.). The test compounds were administered at a dose range of 2 to 4 mg/kg, i.p., to each of six animals per test, 60 minutes following pyloric ligation and 30 minutes prior to aspirin administration (375 mg/kg, p.o.) in 2 ml of artificial gastric juice (USP). One compound was also treated intraduodenally. The rats were sacrificed 60 minutes after aspirin administration by cervical dislocation. The volume of the gastric contents was determined and compared against that produced with the same amount of aspirin for change in volume. Incidence and severity of gastric mucosal bleeding were also determined using an arbitrary grading system on a score of 0 to 40 by a pharmacologist who was unaware of the treatment schedule and results reported as the Gastric Bleeding Index. A score of zero would represent no mucosal hemorrhage and a score of forty represents maximal hemorrhage seen in gastric mucosa of rats exposed to 375 mg/kg dose of aspirin for 60 minutes (Gradation between 0 to 40 is on an even scale). The protective effect of two representative phenylalkylamine compounds of Formula I at 2 and 4 mg, i.p. and i.d. are summarized in Table 1. The data also show that reduction in bleeding is not necessarily dependent on reduction in gastric secretion.

EXAMPLES 3 TO 7 (PHENYLALKYLUREAS)

Phenylalkylurea compounds were tested intraperitoneally by the procedure given in Examples 1 and 2 at dosages of 16 to 100 mg/kp i.p. for effect on aspirin-induced bleeding in rats. The protective results are summarized in Table 2. The data also show that reduction in bleeding is not necessarily dependent on reduction in gastric secretion.

use of the combination of this invention is derived by administering the phenylalkylamine and phenylalkylurea compounds about 1–2 hours prior to the start of the administration of the combination of the protective, remedial and ameliorating effect of the phenylalkylamine and phenylalkylurea compounds is thus maximized. The combination may be given orally and simultaneously or separately. The phenylalkylamine and phenylalkylurea compounds may be given in injectable form prior to and during oral administration of aspirin. It is not necessary that the phenylalkylamine and phenylalkylurea compounds and aspirin be given at precisely the same time of the day, the important requisite being that blood levels of the compounds be sufficiently high to effectively combat the ulcerative effect of aspirin on the gastric tissue of the mammalian stomach. Generally, however, once the preadministration period for the phenylalkylamine and phenylalkylurea compound has passed, in order to insure that administration of the compounds is not neglected, the surest procedure is to administer the combination orally in mixtures such as, for example, powders, slurries or layered tablets; therefore, this procedure and a composition based on the combination represent preferred embodiments of the invention.

According to the present invention as disclosed hereinabove, it has been found that bleeding and ulceration of the stomach caused by aspirin therapy is minimized when the phenylalkylamine and phenylalkylurea compounds of Formula I are also administered in a ratio of

TABLE I

Effect of Phenylalkylamine Compounds of Formula 1 on Aspirin-Induced Bleeding in Rats

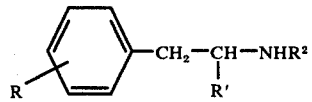

| Example (Compound No.) | R | $R^1$ | $R^2$ | Vol. % Change In Gastric Secretion at 2 mg/kg | at 4 mg/kg | Gastric Bleeding Index at 2 mg/kg | at 4 mg/kg | Percent Decrease In Mucosal Bleeding vs. Controls at 2 mg/kg | at 4 mg/kg |
|---|---|---|---|---|---|---|---|---|---|
| 1 (as HCl salt),IP | $3CF_3$ | $CH_3$ | $C_2H_5$ | −4.3 | −7.1 | 17.5 | 5.8 | −47.4 | −82.6 |
| 2 (as HCl salt),IP | $3CF_3$ | $CH_3$ | H | −3.4 | −32.2 | 1.7 | 0 | −94.3 | −100.0 |
| ID | | | | ca +10 | ca −15 | 11.7 | 0 | −62.0 | −97.0 |

(a) 6 rats each compound, each dosage amount, all rats received 375 mg/kg aspirin
(b) Gastric bleeding index for controls receiving 375 mg/g aspirin was 30–33

TABLE 2

Effect of Phenylalkylurea Compounds of Formula I on Aspirin-Induced Gastric Ulceration in Rats (a)

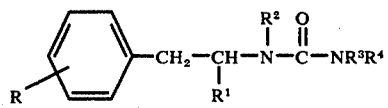

| Example (Compound No.) | R | $R^1$ | $R^2$ | $R^3$ | $R^4$ | Vol % Decrease in Gastric Secretion at 32 mg/kg | at 100 mg/kg | Gastric Bleeding Index (b) at 32 mg/kg | at 100 mg/kg | Percent Decrease In mucosal Bleeding vs. Control at 16 mg/kg | at 32 mg/kg | at 100 mg/kg |
|---|---|---|---|---|---|---|---|---|---|---|---|---|
| 3 | H | $CH_3$ | $CH_3$ | H | H | — | −55 | — | 2 | — | — | −92 |
| 4 | $3$-$CF_3$ | $CH_3$ | H | H | H | −14.3 | — | — | 0 | — | — | −100 |
| 5 | $3$-$CF_3$ | $CH_3$ | $C_2H_5$ | H | H | −34.0 | — | 2 | — | −54 | −95 | — |
| 6 | $3$-$CF_3$ | $CH_3$ | $C_2H_5$ | H | $C_2H_5$ | −11.0 | — | 9 | — | −71 | −71 | — |
| 7 | H | $CH_3$ | $CH_3$ | H | $C_2H_5$ | — | −48 | — | 3 | — | — | −89 |

(a) 6 rats each compound, each dosage amount. All rats received 375 mg/kg aspirin
(b) Gastric bleeding index for controls receiving 375 mg/kg aspirin was 29–33.

Methods of Administration

The combination of aspirin and phenylalkylamines and phenylalkylurea compounds useful in this invention is administered to a variety of mammals including humans, dogs, cats and horses suffering from inflammatory symptoms associated with chronic and acute rheumatoid and degenerative joint disease and other manifestations such as bursitis. The greatest benefit from in parts by weight of about 0.005 to about 0.5 parts per weight of aspirin. The amount of aspirin contained in the combinations or compositions of this invention administered on a daily basis varies from about 20 to 200 mg/kg body weight. Thus, for example, on a daily basis subjects receiving the combination at the highest ratio of a phenylalkylamine and phenylalkylurea compound to aspirin at its upper dosage range would receive on a daily basis 100 mg/kg phenylalkylamine and phenylalkylurea compound and 200 mg/kg aspirin. Subjects treated with the more active phenylalkylamine compounds such as fenfluramine and norfenfluramine would require considerably less than the maximum amount. In general, the pretreatment with the compounds about 1-2 hours prior to start of aspirin therapy may vary from about 0.10 to about 100 mg/kg body weight.

The choice of ratio within the range of about 0.005 to about 0.5 parts by weight compound of Formula I aspirin used in any combination or composition on a variety of subjects will depend somewhat on the species of chemical of Formula I used. It will also depend on such factors as sensitivity of the subject to aspirin and to species of mammal under treatment.

When the combinations of this invention are administered as a composition the mixture will be in a form suitable for oral use, for example, as tablets, hard or soft capsules, aqueous or oily suspensions, dispersible powders or granules, emulsions, hard or soft capsules or syrups or elixirs. The compositions may be prepared according to any known method for the manufacture of pharmaceutical compositions and such compositions may contain one or more agents selected from sweetening agents, flavouring agents, preserving agents and coloring agents in order to provide a pharmaceutically elegant and palatable preparation. Tablets contain the active ingredient in admixture with nontoxic pharmaceutically acceptable excipients which are suitable for the manufacture of tablets. These excipients may be, for example, inert diluents such as lactose, calcium or sodium phosphate, calcium or sodium carbonate, granulating and disintegrating agents such as maize, starch or alginic acid and its salts; binding agents, for example, starch, gelatin, or acacia and lubricating agents, for example, magnesium stearate, stearic acid or talc. The tablets may be coated by known techniques to delay disintegration and absorption in the gastrointestinal tract and thereby provide a sustained action over a longer period. For example, monostearate or glyceryl distearate or a waxy material may be enclosed in hard gelatin capsules mixed therein with an inert solid diluent, for example, calcium carbonate, calcium phosphate, lactose, magnesium stearate or Kaolin, or in soft gelatin capsules in which the active ingredient is mixed with a liquid carrier such as water or an oily medium, for example, vegetable oil, or mineral oil.

Aqueous suspensions containing the combinations with excipients suitable for the manufacture of aqueous suspensions may be used. Suitable excipients are suspending agents, for example, sodium carboxyethylcellulose, methylcellulose, hydroxypropylmethylcellulose, sodium alginite, polyvinylpyrrolidone, gum tragacynth and acacia. Dispersing agents included may be naturally occurring phosphatides such as lecithin, condensation products of an alkalene oxide with fatty acids, for example, polyoxyethylene stearate, condensation products of ethylene oxide with long chain alipheter alcohols, for example, heptadecoethyleneoxycetanol, condensation products of ethylene oxide with partial esters derived from fatty acids and a hexitol, for example, polyoxyethylene sorbits, mono-oleate, or condensation products of ethylene oxide with partial esters derived from fatty acids and hexitol anhydrides, for example, polyoxyethylene sorbitan mono-oleate. The said aqueous suspension may also contain preservatives, for example, ethyl or n-propyl-p-hydroxybenzoate, coloring agents, flavoring agents, sweetening agents such as sucrose or saccharin.

Oily suspensions may be formulated by suspending the aspirin and the ulcer ameliorating agent of Formula I in a vegetable oil, for example, a mineral oil, olive oil, coconut oil, or the like. The oily suspensions may contain a thickening agent such as wax or waxy alcohols. Flavoring and sweetening agents may be added to provide oral preparations which are palatable. Antioxidants such as ascorbic acid may be added as preservatives.

Dispersible powders and granules of anti-inflammatory agent and ameliorating agent suitable for preparation of oral dosage forms which are aqueous suspensions when water is added are provided when dispersing agents, suspending agents, and preservatives are admixed. Suitable dispersing agents and suspending agents are exemplified by those already mentioned above. Sweetening, flavoring and coloring agents may also be present.

Compositions containing the combinations of this invention may also be in the form of oil-in-water emulsions. The oily phase may be an edible oil such as the oils already described above for preparing oily suspensions. Suitable emulsifying agents may be naturally-occurring gums, for example, gum acacia or gum tragacanth, naturally-occurring phosphatides, for example, soy bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

Syrups and elixirs may be formulated with sweetening agents, for example, glycerol, sorbitol or sucrose. Such formulations may also contain a demulcent, a preservative and flavoring and coloring agents.

Alternately, according to the method of this invention, aspirin in any form whatsoever and a compound of Formula I in any pharmaceutically suitable form whatsoever, such as tablets, capsules, suspensions, etc., may be administered concomitantly to a mammalian subject in need of treatment for inflammation for the purpose of ameliorating the undesirable side effects of aspirin and the compound in any pharmaceutically suitable form whatsoever, such as tablets, suspensions, capsules may be administered preceding said concomitant treatment for ulcer and hemorrhagic ameliorating effects which would otherwise occur due to side effects of aspirin therapy.

For veterinary oral use, the combination of aspirin and compounds of Formula I are conveniently prepared in tablets and capsules for unit dosage form of administration or in the form of powders and granules for admixing with food.

The tablets and capsules for veterinary use are generally prepared as described hereinabove and in the formulations to follow and will be commensurate in dosage size to the size of the animal.

The powders and granules for admixing with food suitable for animals are conveniently prepared as hereinabove described or in the form of a food premix. The food premix which can be quite dilute can comprise the combinations of this invention in admixture with an edible pharmaceutical diluent such as starch, oatmeal, flour, calcium carbonate, talc, dried fish meal and dried meat meals. The powders or the prepared premix are then conveniently added to the regular feed, thereby providing the anti-inflammatory action of aspirin but without high incidence of bleeding and ulceration due to the ameliorating effects of the compounds during the course of feeding. Granules of the combination of this invention may be prepared and coated for better reception in food by certain mammals which exhibit "finicky" eating habits such as cats and dogs.

The term "unit dosage form" as used in the specification and claims refers to physically discrete units suitable as unitary dosages for human subjects and animals, each unit containing a predetermined combination of aspirin and the ulcer ameliorating compound calculated to produce the desired therapeutic effect in association with the required pharmaceutical diluent, carrier or vehicle. The specifications for the novel preferred unit dosage forms wherein the said combination is used are dictated by and directly dependent on (a) the effective amount of aspirin required for control of given symptoms and the sensitivity of the subject to the aspirin in the requirement of amount of ameliorating agent needed as disclosed hereinabove, (b) the limitations inherent in the art of compounding such active combinations for therapeutic use in humans and animals as disclosed in detail in this specification, these being features of the present invention. Examples of suitable unit dosage forms in accord with this invention are tablets, capsules, pills, powder pockets, granules, segregated multiples of any of the foregoing including the aspirin and the phenylalkylamine and phenylalkylurea compound and other forms as herein described.

It will be understood, however, that the specific dose level for any particular patient will depend upon a variety of factors, including the activity of the aspirin in a given subject and the ameliorating effect of the compounds of Formula I employed, the age, body weight, general health, sex, diet, mammalian specie, time of administration, and the severity of the particular disease undergoing therapy. In general, the dosage regimen in carrying out the methods of this invention is that which ensures maximum therapeutic response with maximum protection to the subject against side effects of the contained aspirin and thereafter is the minimum effective level which continues to provide relief. It will also be understood that while the combinations of the method of this invention are preferably prepared in unit dosage form containing both the ulcer ameliorating agent and the aspirin, the method of the invention also encompasses separate administration of these agents to subjects suffering from the symptomatic problems in subjects in need of aspirin therapy, particularly of arthritic type disease, in unit dosage form of said agents. The method also encompasses preadministration of the ulcer ameliorating compounds of Formula I at least one to two hours prior to the period of beginning of administration of the aspirin, be it in combined composition with the ulcer ameliorating compound of this invention or be it administered separately but concomitantly with said ameliorating compound.

The compositions of this invention which are used in the co-administration of both aspirin and phenylalkylamine and phenylalkylurea compounds in the same unit dosage form suitable for human use but which may also be suitable for animals in these preparations are illustrated by the following examples for human administration which are not intended to be limiting within the scope of the invention in any way.

Formulations
Example 1-F (1) Capsules

Typical formulations for encapsulation are:

(a)

| | Per capsule, mg |
|---|---|
| Aspirin | 325 |
| 1-(α-methyl-3-trifluoro-methylphenethyl)urea | 75 |
| Lactose | 200 |
| Starch | 2 |
| Total | 612 |

(b)

| | |
|---|---|
| Aspirin | 325 |
| 1-(α-methyl-3-trifluoro-methylphenethyl)urea | 150 |
| Lactose | 150 |
| Magnesium stearate | 2 |
| Total | 627 |

(c)

| | |
|---|---|
| Aspirin | 325 |
| 2-amino-1-(3 trifluoro-methylphenyl)propane | 2 |
| Lactose | 200 |
| Magnesium stearate | 2 |
| Total | 529 |

Example 2-F (2) Tablets

Typical formulations for tableting are:

(a)

| | Per tablet, mg |
|---|---|
| Aspirin | 325 |
| 1-(α-methyl-3-trifluoro-methylphenethyl)urea | 100 |
| Alginic acid | 20 |
| Calcium and ammonium alginate | 40 |
| Starch | 50 |
| Lactose | 60 |
| Magnesium stearate | 2 |
| Total | 597 |

(b)

| | |
|---|---|
| Aspirin | 325 |
| 2-amino-1-(3-trifluoro-methylphenyl)propane | 2 |
| Alginic acid | 20 |
| Calcium and ammonium alginate | 40 |
| Starch | 50 |
| Lactose | 60 |
| Magnesium stearate | 2 |
| Total | 699 |

The compounds are thoroughly blended and tableted.

Example 3-F (3) Suspensions

A typical formulation for suspension is:

| | |
|---|---|
| Aspirin | 375 |
| 1-(α-methyl-3-trifluoro-methylphenethyl)urea | 100 |
| Polysorbate | .1 |
| Methylester of parahydroxy-benzoate | 0.3 |
| Sodium chloride | 1.0 |
| Distilled water | 523.6 |
| Total | 1000.0 |

All components except water are finely divided to less than 200 mesh size and shaken with the water prior to the time of use.

What is claimed is:

1. The method of treating inflammatory conditions in mammals which comprises administering to said mammals an effective amount of aspirin and a phenylalkylurea having the formula:

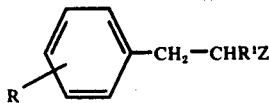

wherein;
Z is selected from the group consisting of

R is selected from the group consisting of hydrogen, chlorine, bromine, fluorine, lower-alkoxy and trifluoromethyl, $R^1$, $R^2$, $R^3$ and $R^4$ are selected from the group consisting of hydrogen and lower-alkyl.

2. The method of claim 1 wherein the compound is 1-methyl-1-(α-methylphenethyl)urea.

3. The method of claim 1 wherein the compound is 1-(α-methyl-3-trifluoromethylphenethyl)urea.

4. The method of claim 1 wherein the compound is 1-ethyl-1-(α-methyl-3-trifluoromethylphenethyl)urea.

5. The method of claim 1 wherein the compound is 1,3-diethyl-1-(α-methyl-3-trifluoromethylphenethyl)urea.

6. The method of claim 1 wherein the compound is 3-ethyl-1-methyl-1(α-methylphenethyl)urea.

7. An anti-inflammatory composition for oral administration comprised of
 a. a combination of 67 to 99.5 weight % aspirin, and 0.5 to 33.0 weight % of a phenylalkylurea selected from those having the formula

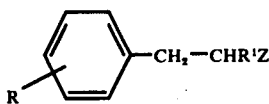

wherein;
Z is selected from the group consisting of $$NR^2CON\diagup^{R^3}_{R^4}$$

R is selected from the group consisting of hydrogen, chlorine, bromine, fluorine, lower-alkoxy and trifluoromethyl, $R^1$, $R^2$, $R^3$ and $R^4$ are selected from the group consisting of hydrogen and lower-alkyl and b. A pharmaceutically acceptable carrier therefor.

8. A composition of claim 7 wherein the compound is 1-methyl-1-(α-methylphenethyl)urea.

9. A composition of claim 7 wherein the compound is 1-(α-methyl-3-trifluoromethylphenethyl)urea.

10. A composition of claim 7 wherein the compound is 1-ethyl-1-(α-methyl-3-trifluoromethylphenethyl)urea.

11. A composition of claim 7 wherein the compound is 1,3-diethyl-1-(α-methyl-3-trifluoromethylphenethyl)urea.

12. A composition of claim 7 wherein the compound is 3-ethyl-1-methyl-1(α-methylphenethyl)urea.

13. A composition of claim 7 in the form of a tablet, aqueous or oily suspension, dispersible powder or granules, emulsion, hard or soft capsule, syrup or elixir.

14. A composition of claim 7 in the form of a food premix for administration to animals.

* * * * *